United States Patent
Lange et al.

(12) 
(10) Patent No.: US 6,689,889 B2
(45) Date of Patent: *Feb. 10, 2004

(54) CHROMATOGRAPHIC SEPARATION OF ENANTIOMERS OF LACTONES

(75) Inventors: Walter Lange, Leverkusen (DE); Rolf Grosser, Leverkusen (DE); Burkhard Köhler, Leverkusen (DE); Stefan Michel, Walsrode (DE); Bruno Bömer, deceased, late of Bergisch Gladbach (DE); by Karin-Elfriede Bömer, executor, Bergisch Gladbach (DE); by Guido Martin Bömer, executor, Bonn (DE); by Felix Marcel Bömer, executor, Bergisch Gladbach (DE); Uwe Zweering, Leverkusen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 212 days.

This patent is subject to a terminal disclaimer.

(21) Appl. No.: 09/757,919

(22) Filed: Jan. 10, 2001

(65) Prior Publication Data

US 2002/0133017 A1 Sep. 19, 2002

Related U.S. Application Data

(62) Division of application No. 09/380,332, filed as application No. PCT/EP98/01788 on Mar. 26, 1998, now Pat. No. 6,274,736.

(30) Foreign Application Priority Data

Apr. 8, 1997 (DE) .......................................... 197 14 343

(51) Int. Cl.$^7$ ............................................. C07D 405/06
(52) U.S. Cl. ..................................... 546/282.1; 210/656
(58) Field of Search ........................ 546/282.1; 210/656

(56) References Cited

U.S. PATENT DOCUMENTS

| | | |
|---|---|---|
| 4,619,970 A | 10/1986 | Okamoto et al. |
| 4,855,481 A | 8/1989 | Guindon et al. |
| 4,897,490 A | 1/1990 | Sit et al. |
| 4,914,159 A | 4/1990 | Bomer et al. |
| 4,970,313 A | 11/1990 | Wess et al. |
| 4,992,429 A | 2/1991 | Ullrich et al. |
| 5,177,080 A | 1/1993 | Angerbauer et al. |
| 5,273,995 A | 12/1993 | Roth |
| 5,274,167 A | 12/1993 | Lange et al. |
| 5,502,199 A | 3/1996 | Angerbauer et al. |
| 5,868,938 A | 2/1999 | Bomer et al. |

FOREIGN PATENT DOCUMENTS

| | | |
|---|---|---|
| EP | 0 155 637 A | 9/1985 |
| EP | 0 183 132 A | 6/1986 |
| EP | 0 319 847 A | 6/1989 |
| EP | 0 379 917 A | 8/1990 |
| EP | 0 409 281 A | 1/1991 |
| EP | 0 617 019 A | 9/1994 |
| EP | 0 780 408 A | 6/1997 |
| WO | WO 92 14692 A | 9/1992 |

OTHER PUBLICATIONS

XP002073359 New Chiral Polyamide Stationary Phase for Chromatographic Enantiomer Sepaaration, Alt et al., Agnew. Chem. Int. Ed. Eng., Bd. 30 Nr. 12, 1991, Seiten 1662–1664.

V.R. Meyer, Praxis der Hochleistungsflussigchromatographie, Salle + Sauerlander, 6. Aufl. 1990, S 79 ff.

Arlt et al.: "New chiral polyamid stationary phases for chromatografic enantiomer separation" Agnew. Chem. Int. Ed. Eng., vol. 30, No. 12, 1991, pp. 1662–1664, XP002073359.

*Primary Examiner*—Jane Fan
(74) *Attorney, Agent, or Firm*—Norris McLaughlin & Marcus

(57) ABSTRACT

The present invention relates to the use of optically active polymers of N-acryloyl-phenylalanine neomenthylamide as such, in crosslinked form and/or in carrier-bonded form as stationary phases for the chromatographic separation of enantiomers of lactones.

4 Claims, No Drawings

CHROMATOGRAPHIC SEPARATION OF ENANTIOMERS OF LACTONES

This application is a div. of Ser. No. 09/380,332 Sep. 3, 1999 U.S. Pat. No. 6,274,736 which is a 371 of PCT/EP98/01788 Mar. 26, 1998.

The present invention relates to the use of optically active polymers of N-acryloyl-phenylalanine neomenthylamide as such, in crosslinked form and/or in carrier-bonded form as stationary phases for the chromatographic separation of enantiomers of lactones.

EP 379 917 describes chiral stationary phases which are derived from N-(meth)-acryloylamino acid derivatives and which are suitable for the separation of enantiomers, inter alia also of lactone derivatives. Bead polymers are preferably employed as the separating phases.

It is furthermore known from EP 617 019 that (±)-trans-(E)-6-[2-(2,6-diisopropyl-4-(4-fluorophenyl)-3-methoxymethyl-pyrid-5-yl)-ethenyl]-3,4,5,6-tetrahydro-4-hydroxy-2H-pyran-2-one (Ii) can be separated into the enantiomers by chromatography on chiral stationary phases. As described in EP 617 019 and 491 226, this lactone is converted into sodium 3R,5S-(+)-erythro-(E)-7-[4-(4-fluorophenyl)-2,6-diisopropyl-5-methoxymethyl-pyrid-3-yl]-3,5-dihydroxy-hept-6-enoate (A) which inhibits cholesterol biosynthesis and can be employed in medicaments for the treatment of lipoproteinaemia.

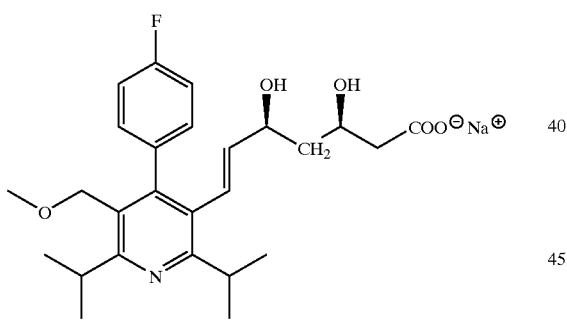

(A)

EP 617 019 describes that this separation can advantageously be carried out by chromatography on chiral stationary phases, such as are mentioned in EP 379 917. Polymers of S-phenylalanine d-menthyl ester are mentioned there as particularly suitable phases.

However, it has now been found, surprisingly, that the separation of lactone derivatives is particularly efficient if the optically active polymers are derivatives of amino acid amides. Polymers of N-acryloyl-phenylalanine neomenthylamide are particularly suitable.

The invention therefore relates to the use of optically active polymers of N-acryloyl-S-phenylalanine d-neomenthylamide or of the enantiomer thereof as such, in crosslinked form and/or in carrier-bonded form as stationary phases for the chromatographic separation of enantiomers of lactones of the general formula (I)

(I)

wherein

R represents an organic radical and

X represents —CH$_2$—CH$_2$— or —CH=CH—.

The lactones (or the ring-opening products) of the general formula (I) typically act as HMG-CoA reductase inhibitors. Such compounds are suitable, for example, for the treatment of hyperlipoproteinaemia or arteriosclerosis.

Preferred compounds of the formula (I) are HMG-CoA reductase inhibitors in which the radical R is a derivative of an aromatic or partly saturated carbocyclic ring having 6 or 12 carbon atoms, an indole derivative, a pyridine derivative, a pyrrole derivative or an ethene derivative.

Particularly preferred examples for this are the following compounds:

(Ia)

(Ib)

(Ic)

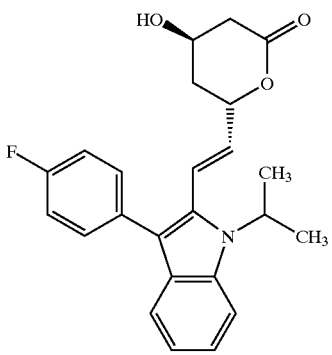

(Id)

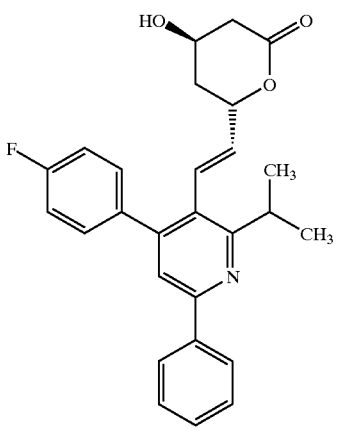

(Ie)

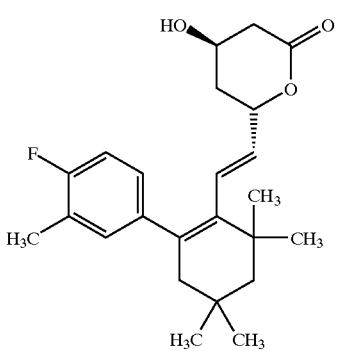

(If)

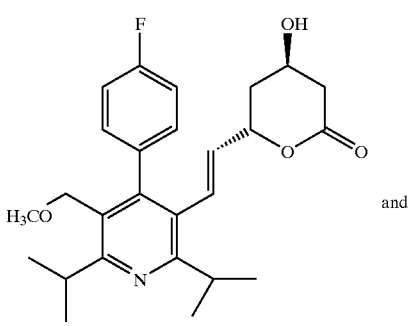

and (Ii)

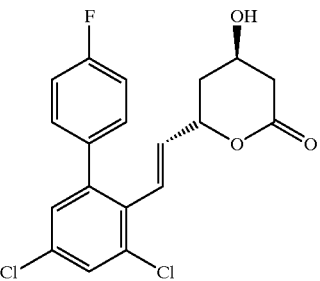

(Ik)

According to an especially preferred embodiment, the invention relates to the use of optically active polymers of N-acryloyl-S-phenylalanine d-neomenthylamide or of the enantiomer thereof as such, in crosslinked form and/or in carrier-bonded form as stationary phases for the chromatographic separation of enantiomers of (±)-trans-(E)-6-[2-(2, 6-diisopropyl-4-(4-fluorophenyl)-3-methoxymethyl-pyrid-5-yl)-ethenyl]-3,4,5,6-tetrahydro-4-hydroxy-2H-pyran-2-one.

The invention furthermore also relates to a process for the chromatographic separation of enantiomers of lactone compounds of the general formula (I), characterized in that the corresponding enantiomer mixture is separated into the enantiomers by means of an optically active polymer of N-acryloyl-S-phenylalanine d-neomenthylamide or of the enantiomer thereof as the chiral stationary phase, using a suitable mobile phase, the optically active polymer being employed as such, in crosslinked form and/or in carrier-bonded form.

Which lactone compounds of the general formula (I) can preferably be separated into the enantiomers by this process has already been mentioned above.

The chiral stationary phases used according to the invention are derived from N-acryloyl-S-phenylalanine d-neomenthylamide or from its enantiomer N-acryloyl-R-phenylalanine l-neomenthylamide. The phases derived from N-acryloyl-S-phenylalanine d-neomenthylamide are preferred.

N-Acryloyl-S-phenylalanine d-neomenthylamide or its enantiomer can be prepared by known processes, for example as described in U.S. Pat. No. 5,274,167/EP 379 917.

The optically active N-acryloyl-phenylalanine neomenthylamide polymer used according to the invention is preferably employed in the form of crosslinked insoluble but swellable polymers or in a form bonded to finely divided inorganic carrier materials. It can also be prepared as a linear polymer which is soluble in suitable organic solvents. It is furthermore possible to incorporate 0.1 to 60, preferably 0.1 to 20 mol % of copolymerizable non-chiral monomers into the polymer.

The crosslinked polymers are preferably present in the form of finely divided beads having a particle diameter of 5 to 200 μm, preferably 10–100 μm. They can be prepared in a manner known per se by polymerization with the addition of a suitable crosslinking agent, for example as described in U.S. Pat. No. 5,274,167/EP 379 917.

The degree of swelling of the (bead) polymers can be adjusted by the nature and amount of the crosslinking agent (of the crosslinking agents).

For use in practice, (bead) polymers having a degree of swelling (Q) of 1.1 to 10, preferably 2.0 to 7.0, have proved suitable.

$$Q = \frac{\text{resin volume (swollen)}}{\text{resin volume (non-swollen)}}$$

The polymer of N-acryloyl-S-phenylalanine d-neomenthylamide or the enantiomer thereof is particularly preferably employed as the stationary phase in a form bonded to finely divided inorganic carrier materials, preferably to silica gel.

Coating of the silica gels with polymerization-active groups by means of free radicals and the polymerization can be carried out by methods known per se.

For example, the optically active polymer can be taken up onto the silica gel by adsorbing it physically or fixing it covalently. The latter can be effected by coating the silica gel surface with polymerizable groups and then carrying out a copolymerization with the optically active monomer. Polymerization of the optically active monomer in the presence of silica gel diol phases, which have been esterified with (meth)acrylic acid, is also widely applicable. Suitable processes are described, for example, in EP 379 917 and EP 282 770.

According to a particularly preferred process, the silica gel is first coated with mercapto groups (SH units) and then reacted with the optically active monomer under polymerization conditions (cf. our European patent application also pending, Application No. 96 119 045.1).

The silica gel modified on the surface with SH units is expediently obtained by reacting the starting material with a compound which contains at least one mercapto group. Suitable derivatizing reagents are known in principle (V. R. Meyer, Praxis der Hochleistungsflüssigchromatographie [High performance liquid chromatography practice], Salle+ Sauerländer, 6th Edition 1990, page 79 et seq. and the literature cited therein); they have the general form Q-L-SH, wherein Q represents a reactive group which can react with the OH groups of the silica gel and L represents a spacer group which is inert under the corresponding conditions and ensures the necessary distance between the silica gel and SH group.

Silica gels are preferably coated by reaction of a non-modified silica gel with a silane of the form $Z_1Z_2Z_3$Si-L-SH, wherein $Z_1$, $Z_2$ and $Z_3$ independently of one another represent alkyl having up to 4 carbon atoms, halogen, alkoxy having up to 4 carbon atoms or hydroxyl and L represents an optionally substituted alkylene chain having up to 7 carbon atoms.

The reaction can be carried out under base catalysis or in an acid medium. The silica gel is usually reacted in a ratio of the functionalization reagent to silica gel of 1:20 to 1.2:1. Silica gels which comprise 0.1% to 5%, particularly preferably 0.5% to 3% of sulphur in the form of SH groups and in which the optically active polymer is bonded to the mercapto groups of the modified silica gel result.

According to the abovementioned process, in a first step the silica gel is coated with a mono-, di- or trialkoxy- or mono-, di- or trichlorosilane compound which is capable of polymerization or graftable, preferably with mercaptopropyl-trimethoxysilane, mercaptopropyl-triethoxysilane, mercaptopropyl-methyl-dimethoxysilane, bis(3-trimethoxysilylpropyl) tetrasulphone, thiocyanatopropyltrimethoxysilane, thiocyanatopropyltriethoxysilane, bis(3-triethoxysilylpropyl)tetrasulphone, trimethoxy-vinylsilane, triethoxy-vinylsilane, trichlorovinylsilane, dimethoxy-methyl-vinylsilane, dichloro-methyl-vinylsilane, chloromethylvinylsilane, methoxy-dimethyl-vinylsilane, methacryloyloxypropyl-trimethoxysilane, methacryloyloxypropyl-triethoxysilane, glycidyloxypropyl-triethoxysilane or glycidyloxypropyl-trimethoxysilane, particularly preferably with the abovementioned mercaptosilanes. Mercaptopropyl-trimethoxysilane and mercaptopropyltriethoxysilane are especially preferred. The mono-, di- or trialkoxy- or mono-, di- or trichlorosilane compound which is capable of polymerization or graftable is added in amounts of 5 to 120% by weight, based on the silica gel. Preferably, 5 to 15% by weight of the mercaptosilanes and 80 to 120% by weight of the vinylsilanes is employed.

As the second step, the free-radical polymerization is carried out by addition of N-acryloyl-phenylalanine neomenthylamide in amounts of 10 to 100% by weight, preferably 30 to 60% by weight, based on the coated silica gel, to the suspension of the coated silica gel in a solvent, such as, for example, toluene, benzene, chlorobenzene, chloroform, isopropanol, n-butanol, cyclohexanol, MIBK, ethyl acetate or dioxane, 0.5 to 10% by weight, preferably 1 to 5% by weight, of a free-radical chain initiator, such as, for example, azobisisobutyronitrile or benzoyl peroxide, based on the amount of N-acryloylamino acid neomenthylamide, being added and the mixture being heated at 56 to 110° C. for 1 to 24 hours.

Silica gels used according to the invention are spherical or irregular and have an average particle diameter of 1 to 200, preferably 5 to 50μ. They are commercially obtainable, for example from the companies Macherey und Nagel, Merck, YMC or Akzo.

Suitable mobile phases for the separation of the racemate are all the customary organic solvents and solvent mixtures which are capable of dissolving the racemate. If the optically active polymer is bonded chemically to the silica gel, there is no restriction on the organic solvent to be used caused by the chiral stationary phase, since the polymer cannot be washed out.

Examples of mobile phases which may be mentioned here are: hydrocarbons, such as benzene, toluene, xylene, pentane, hexane and heptane, ethers, such as diethyl ether, t-butyl methyl ether, dioxane and tetrahydrofuran, halogenohydrocarbons, such as methylene chloride, chloroform and chlorobenzene, alcohols, such as n-butanol, n-propanol, i-propanol, ethanol and methanol, acetone, methyl ethyl ketone, acetonitrile, ethyl acetate, dimethylformamide and mixtures of the abovementioned solvents. Particularly preferred mobile phases are mixtures of toluene with tetrahydrofuran in a ratio of 10:1 to 1:10, preferably 5:1 to 1:5.

The separations are as a rule carried out under the customary conditions of separations by liquid chromatography. They can be carried out both on an analytical scale and on a preparative scale.

An efficient separation of the compounds of the general formula (I) is achieved on an individual column filled with a silica gel onto which an optically active polymer of N-acryloyl-(S)-phenylalanine d-neomenthylamide or of the enantiomer thereof is bonded. The separation is particularly advantageous if this is not employed by batch operation on an individual column but in a continuous process designed according to the simulated moving bed process, as described, for example, in EP 586 385.

The capacity of the polymers for the separation of the racemate is expressed by the capacity ratios ($k_{1(2)}'$ values) for the two enantiomers (1) and (2) and the enantioselectivity value α resulting therefrom. These chromatographic parameters are defined as follows:ps
capacity ratio $k_{1(2)}'=(t_{1(2)}-t_{(0)})/t_{(0)}$ and
enantioselectivity value=$\alpha=k_2'/k_1'$
$t_0$=dead time of the column $t_{1(2)}$=retention time of the enantiomer 1 eluted first or, respectively, of the enantiomer 2 eluted later.

EXAMPLES

Example 1

30 g of mercaptopropyltrimethoxysilane, 9 g of p-toluenesulphonic acid and 2.4 ml of water are added to a suspension of 300 g of a dried irregular silica gel having an average particle diameter of 10μ (Polygosil 100/10μ from Macherey & Nagel) in 31 of toluene, and the mixture is heated under reflux for 8 hours. The solid is filtered off with suction over a frit, washed with methylene chloride, with methylene chloride/methanol 1:1 and twice more with methylene chloride and dried under a high vacuum for 24 hours.

Example 2

3 g of the coated silica gel from Example 1 are initially introduced into 12 ml of toluene, 1.2 g of N-acryloyl-L-phenylalanine d-neomenthylamide and 20 mg of azobisisobutyronitrile are added and the mixture is heated at 60° C. for 12 hours. 0.2 g of 2,2-methylene-bis-6,6-dicyclohexyl-4,4-methylphenol and 3 ml of bistrimethylsilylacetamide are then added and the mixture is boiled under reflux for 4 hours. The solid is filtered off with suction over a G4 frit, washed with methylene chloride, methanol/methylene chloride 1:1, toluene, isopropanol and again with methylene chloride and dried under a high vacuum for 10 hours.

3.21 g of a silica gel having a nitrogen content (determined by elemental analysis) of 1.6%, corresponding to a polymer coating of 20.3% by weight, are obtained.

Example 3

Separation Example

The polymers bonded to silica gel (prepared as described in Example 1 and 2) were employed in steel columns (internal diameter 4.6 mm; length 250 mm). Elution was carried out with a toluene/tetrahydrofuran (3:1) mixture. The flow rate of the mobile phase was 1 ml/minute.

| | |
|---|---|
| Racemate: | (±)-trans-(E)-6-[2-(2-6-diisopropyl-4-(4-fluorophenyl)-3-methoxymethyl-pyrid-5-yl)-ethenyl]-3,4,5,6-tetrahydro-4-hydroxy-2H-pyran-2-one (Ii) |
| Relative capacity $k_1'$: | 0.47 |
| Relative capacity $k_2'$: | 2.73 |
| Enantioselectivity α: | 5.82 |

What is claimed is:

1. A process for the chromatographic separation of a mixture of enantiomers of (±)-trans-(E)-6-[2-(2,6-diisopropyl-4-(4-fluorophenyl)-3-methoxymethyl-pyrid-5-yl)-ethenyl]-3,4,5,6-tetrahydro-4-hydroxy-2H-pyran-2-one into separate enantiomers thereof, said process comprising separating the separate enantiomers from a mobile phase comprising said mixture of enantiomers by means of chiral stationary phase comprising A) an optically active polymer selected from the group consisting of an optically active polymer of N-acryloyl-S-phenylalanine d-neomenthylamide and an optically active polymer of an enantiomer of N-acryloyl-S-phenylalanine d-neomenthyl-amide, B) a crosslinked form of said optically active polymer and/or C) a carrier-bonded form of said optically active polymer.

2. The process according to claim 1, wherein the optically active polymer is employed in a form bonded to silica gel.

3. The process according to claim 2, wherein the optically active polymer is bonded via mercapto groups from a correspondingly modified silica gel.

4. The process according to claim 1, wherein a mixture of toluene and tetrahydrofuran is used as the mobile phase.

* * * * *